United States Patent [19]
Dorgan et al.

[11] Patent Number: 6,103,716
[45] Date of Patent: Aug. 15, 2000

[54] PYRIDO(3,2,1-IJ)-1,3,4-BENZOXADIAZINE

[75] Inventors: Roderick John Dorgan, Surrey, United Kingdom; David Walter Gottschall, West Chester, Pa.

[73] Assignee: Pfizer Inc., New York, N.Y.

[21] Appl. No.: 09/101,567

[22] PCT Filed: Oct. 31, 1996

[86] PCT No.: PCT/GB96/02675

§ 371 Date: Sep. 9, 1998

§ 102(e) Date: Sep. 9, 1998

[87] PCT Pub. No.: WO97/27201

PCT Pub. Date: Jul. 31, 1997

[30] Foreign Application Priority Data

Jan. 24, 1996 [GB] United Kingdom .................. 9601356

[51] Int. Cl.[7] ...................... A61K 31/535; C07D 273/00; C07D 273/04
[52] U.S. Cl. .................... 514/229.2; 514/229.2; 544/66
[58] Field of Search .............................. 514/229.2; 544/66

[56] References Cited

U.S. PATENT DOCUMENTS 4,801,584   1/1989   Yokose et al. ......................... 514/183

FOREIGN PATENT DOCUMENTS

WO 0259804   3/1988   WIPO .

*Primary Examiner*—Mukund J. Shah
*Assistant Examiner*—Ben Schroeder
*Attorney, Agent, or Firm*—Peter C. Richardson; Paul H. Ginsburg; E. Victor Donahue

[57] ABSTRACT

A novel compound having antibacterial activity according to the the formula

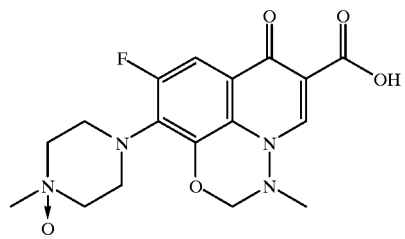

The compound of the present invention may be prepared from (9-fluoro-3-methyl-10-(4-methyl-1-piperazinyl)-7-oxo-2,3-dihydro-7H-pyrido[3,2,1-ij]-1,3,4-benzadiazine-6-carboxylic acid by treatment with an oxidizing agent, such as hydrogen peroxide in the presence of an aqueous inorganic base. Additionally, there are provided methods for treating animals, including humans, suffering from bacterial infections.

6 Claims, No Drawings

PYRIDO(3,2,1-IJ)-1,3,4-BENZOXADIAZINE

The present invention relates to a novel compound, to processes for its production, to pharmaceutical formulations containing it, and to its use in therapy, particularly in the treatment of microbial infections.

EP-A-0 259 804 describes the compound of formula (A):

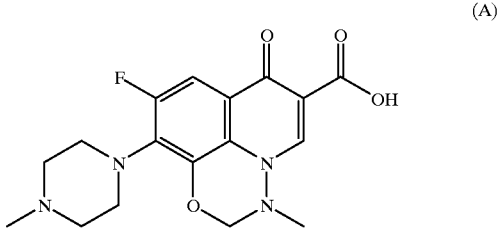

(9-fluoro-3-methyl-10(4-methyl-1-piperazinyl)-7-oxo-2,3-dihydro-7H-pyrido [3,2,1-ij]-1,3,4-benzadiazine-6-carboxylic acid, or marbofloxacin). The compound of formula (A) is reported to have antibacterial activity.

The present invention provides the compound of formula (I):

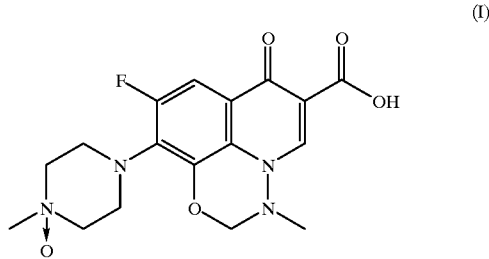

The compound of formula (I) has antibacterial activity and is therefore of use in the treatment and prophylaxis of bacterial infections in humans and animals.

The invention in a second aspect, further provides a process for the production of the compound of formula (I), which comprises treating the compound of formula (A) with an oxidizing agent, more especially an excess of hydrogen peroxide in the presence of an aqueous inorganic base. The process is typically carried out at ambient temperature and monitored by tlc. After filtration, the reaction is quenched by neutralization to pH6. The product is collected by slow filtration, washed, and stored in the dark.

The compound according to the invention is suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of the compound according to the invention may, for example, be used in the preparation of a more pure form of the same compound.

The compound of the invention has antibacterial activity and is useful for the prophylactic and therapeutic treatment of bacterial infections in animals especially mammals, including humans, in particular humans and domesticated animals (including farm animals). The compound may be used for the treatment of infections caused by, among, other organisms, species of Staphylococcus. Streptococcus, Aerococcus, Enterococcus, Micrococcus, Kactobacillus, Bifidobacterium, Clostndium, Eubacterium, Peptococcus, Peptostreptococcus, Propionibacterium, Citrobacter, Campylobacter, Enterobacter, Klebsiella, Proteus, Pseudomonas. Serratia, Salmonella, Shigella, Vibrio, Aeromonas, Haemophilus, Neisseria, Acinetobacter, Alcaligenes, Bordetella, Bacteroids, Fusobacterium, Myocoplasma and other microorganisms.

Accordingly a third aspect of the invention provides the compound of formula (I) for use in medical therapy, in particular for use as an antibacterial agent.

The invention further provides a method of treating a human or animal suffering from a bacterial infection by the administration of an effective amount of the compound of the invention.

A particular method of the invention comprises treating or preventing bacterial infections in non-human animals, more particularly domesticated mammals and birds, such as horses, cattle, swine, sheep, companion animals including dogs and cats, and poultry including chickens. The method comprises administering to the animal via the oral route an antibacterially effective amount of a compound of formula (I):

A further aspect of the invention provides use of a compound of formula (I) in the manufacture of a medicament for use in the treatment or prevention of bacterial infections in non-human animals by administration via the oral route.

The invention further provides a pharmaceutical composition comprising a compound of the formula (I) together with a pharmaceutically acceptable diluent or carrier.

The compound of the invention can be administered alone, but will generally be administered in admixture with a pharmaceutical carrier selected with regard to the intended route of administration and standard pharmaceutical practice. For example, it may be administered orally in the form of a tablet containing such excipients as starch or lactose, or in a capsule or ovule either alone or in admixture with excipients, or in the form of an elixir or suspension containing a flavouring or colouring agent It may be injected parenterally, for example, intravenously, intramuscularly or subcutaneously. For parenteral administration, it is best used in the form of a sterile solution which may contain other substances, for example, enough salts or glucose to make the solution isotonic.

For oral and parenteral administration, it is expected that the daily dosage level of the compound of formula (I) will be from 0.5 to 500, preferably 1 to 300 mg/kg (in divided doses) when administered by either the oral or parenteral route.

No unacceptable toxicological effects are expected when the compound is administered in the above mentioned dosage ranges.

The compounds and compositions according to the invention may be formulated for administration in any convenient way for use in human or veterinary medicine, by analogy with other antibacterial agents.

The tablets and capsules for oral administration may be in unit dosage form, and may contain conventional excipients including, for example, binding agents, for example, syrup, acacia, gelatin, sorbitol, tragacanth, or polyvinylpyrrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, propyleneglycol. The compound, depending on the vehicle and concentration used, may be either suspended or dissolved in the vehicle. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

Compositions according to the invention may also be administered by inhalation. By "inhalation" is meant intranasal and oral inhalation administration.

Appropriate dosage forms for such administration such as an aerosol formulation or a metered dose inhaler, may be prepared by conventional techniques.

Preferably, the compound of formula (I) is administered in admixture with the animal's feedstuff or drinking water. Thus, a further aspect of the invention provides feedstuff or drinking water having a compound of formula (I) mixed therewith, as well as a premix comprising a compound of formula (I) together with a veterinarily acceptable carrier. Suitable carriers include a mixture of a binder, such as polyvinylpyrrollidone, and a filler, such as lactose, which can be extruded, granulated and mixed with or sprinkled on the animals' food. For addition to drinking water, the active is first made up as a concentrate with a liquid carrier, such as gluconolactone.

The following example serves to illustrate the present invention.

EXAMPLE

Marbofloxacin N-oxide

Marbofloxacin (10.87 g, 0.03 moles) was placed in 50 ml of water, and 50% aqueous sodium hydroxide (2.41 g, 1 equivalent) was added, to pH 12.5. The mixture was stirred, and 50% hydrogen peroxide (6.15 g, about 3 equivalents) was added in 15 ml water over several minutes. The reaction mixture was stirred at 22° C. for 100 hr. TLC (silica. $CHCl_3/H_2O/HOAc$, 55:10:5) showed completion of the reaction. The reaction mixture was filtered by gravity to remove any solid matter, and washed three times with water. The filtrate and washings were diluted to 380 ml, stirred, and 10% aqueous acetic acid was added over 15 minutes to a pH of 6.0. The precipitate was stirred at room temperature in the dark for 30 minutes, collected by slow filtration, washed with water (100 ml), then acetone (100 ml) and dried in the dark.

Yield: 11.79 g (100% as hydrate), m.p. 235–238° C., MS (FAB) $M+1^+m/z=379$, 1HNMR (320K. DMSO-d6): 8.75 ppm (s, 1), 7.75 ppm (d, 1), 5.3 ppm (d, 2), 3.9 ppm (m,4), 3.6 ppm (t. 2). 3.4 ppm (d, 2). 3.1 ppm (m, 6).

What is claimed is:

1. Compound of formula (I)

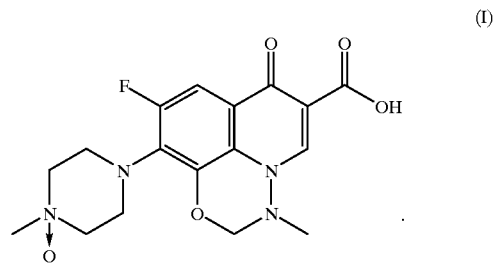

(I)

2. A process for the production of the compound of claim 1 which comprises treating the compound of formula (A)

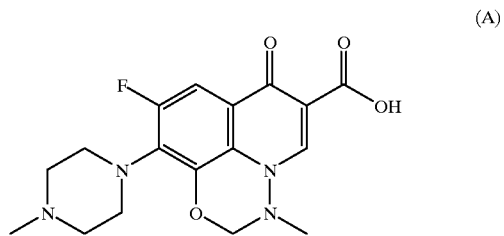

(A)

with an oxidizing agent.

3. The process of claim 2, wherein the compound of formula (A) is treated with an excess of hydrogen peroxide in the presence of an aqueous inorganic base.

4. A method of treating a human or animal for a bacterial infection, that comprises administering an effective amount of the compound of claim 1.

5. The method of claim 4, wherein said antibacterially effective amount of the compound of claim 1 is administered orally.

6. A pharmaceutical composition comprising the compound of claim 1 together with a pharmaceutically acceptable diluent or carrier.

* * * * *